United States Patent [19]
Cohen et al.

[11] Patent Number: 5,952,473
[45] Date of Patent: Sep. 14, 1999

[54] REAGENT AND KIT FOR DETERMINING ISOPRENYLATING ACTIVITY AND INHIBITION THEREOF

[76] Inventors: Louis Hartog Cohen, Voortwijk 10, NL-3621 HR Breukelen; Willem Nieuwenhuizen, Groeneweg 48, NL-3981 CL Bunnik, both of Netherlands

[21] Appl. No.: 08/951,309

[22] Filed: Oct. 16, 1997

Related U.S. Application Data

[63] Continuation-in-part of application No. 08/230,522, Apr. 20, 1994, abandoned.

[30] Foreign Application Priority Data

Apr. 20, 1993 [EP] European Pat. Off. ............. 93201146

[51] Int. Cl.$^6$ ........................... C01K 16/00; G01N 33/53
[52] U.S. Cl. ...................... 530/388.1; 530/810; 530/811; 530/812; 530/813; 530/814; 435/7.1; 435/975
[58] Field of Search ................. 435/7.1, 975; 530/388.1, 530/810, 811, 812, 300, 324, 325, 326, 327, 328, 329, 330, 813, 814, 3

[56] References Cited

U.S. PATENT DOCUMENTS

| | | | |
|---|---|---|---|
| 5,141,851 | 8/1992 | Brown et al. | 435/15 |
| 5,185,248 | 2/1993 | Barbacid et al. | 435/15 |
| 5,366,871 | 11/1994 | Rechsteiner et al. | 435/24 |
| 5,420,245 | 5/1995 | Brown et al. | 530/328 |

FOREIGN PATENT DOCUMENTS

| | | |
|---|---|---|
| 0456180 | 11/1991 | European Pat. Off. . |
| WO91/16340 | 10/1991 | WIPO . |

OTHER PUBLICATIONS

Campbell, in Laboratory Techniques in Biochemistry and Molecular Biology, pub 1991 by Elsevier, NY. pp. 1–49.

Hermanson et al "Immobilized Affinity Ligand Techniques", 1992 by Academic Press Inc, San Diego CA, pp. 137–158.

"A protein geranylgeranyltransferase from bovine brain: Implications for protein prenylation specificity", *Proceedings of the National Academy of Sciences of USA*, vol. 88, Jun. 1991, Washington by K. Yokoyama et al., pp. 5302–5306.

"In vitro identification of a soluble protein: geranylgeranyl transferase from rat tissues", *The Journal of Biological Chemistry*, vol. 266, No. 21, Jul 25, 1991, Baltimore, by A. Joly et al., pp. 13495–13498.

"Sequence dependence of protein isoprenylation", *The Journal of Biological Chemistry*, vol. 266, No. 22, Aug. 5, 1991, Baltimore by S.L. Moores et al., pp. 14603–14610.

"Nonfarnesylated tetrapeptide inhibitors of protein farnesyltransferase", *The Journal of Biological Chemistry*, vol. 266, No. 24, Aug. 25, 1991, Baltimore, by J.L. Goldstein et al., pp. 15575–15578.

"Biochemistry of protein prenylation", *Journal of Lipid Research*, vol. 33, No. 12, Dec. 1992, Bethesda by P.J. Casey, pp. 1731–1740.

*Primary Examiner*—Patricia A. Duffy

[57] ABSTRACT

The invention provides an immobilised oligopeptide for detecting protein prenylation consisting of an oligopeptide containing the amino acid sequence Xad-Xac-Xab-Xaa-OH at its carboxyl-terminus, at least one of Xaa, Xab, Xac and Xad representing cysteine (Cys), said sequence being capable of acting as a substrate for a prenyl transferase catalysing protein prenylation, and being bonded to a solid carrier, preferably at its amino-terminus. The invention further provides a kit for detecting protein prenylation comprising a first immobilised oligopeptide as mentioned above and a second immobilised oligopeptide which differs from said first immobilised oligopeptide in that the cysteine residue is substituted by another amino acid. Also provided are antibodies against the prenylated oligopeptides.

5 Claims, 5 Drawing Sheets

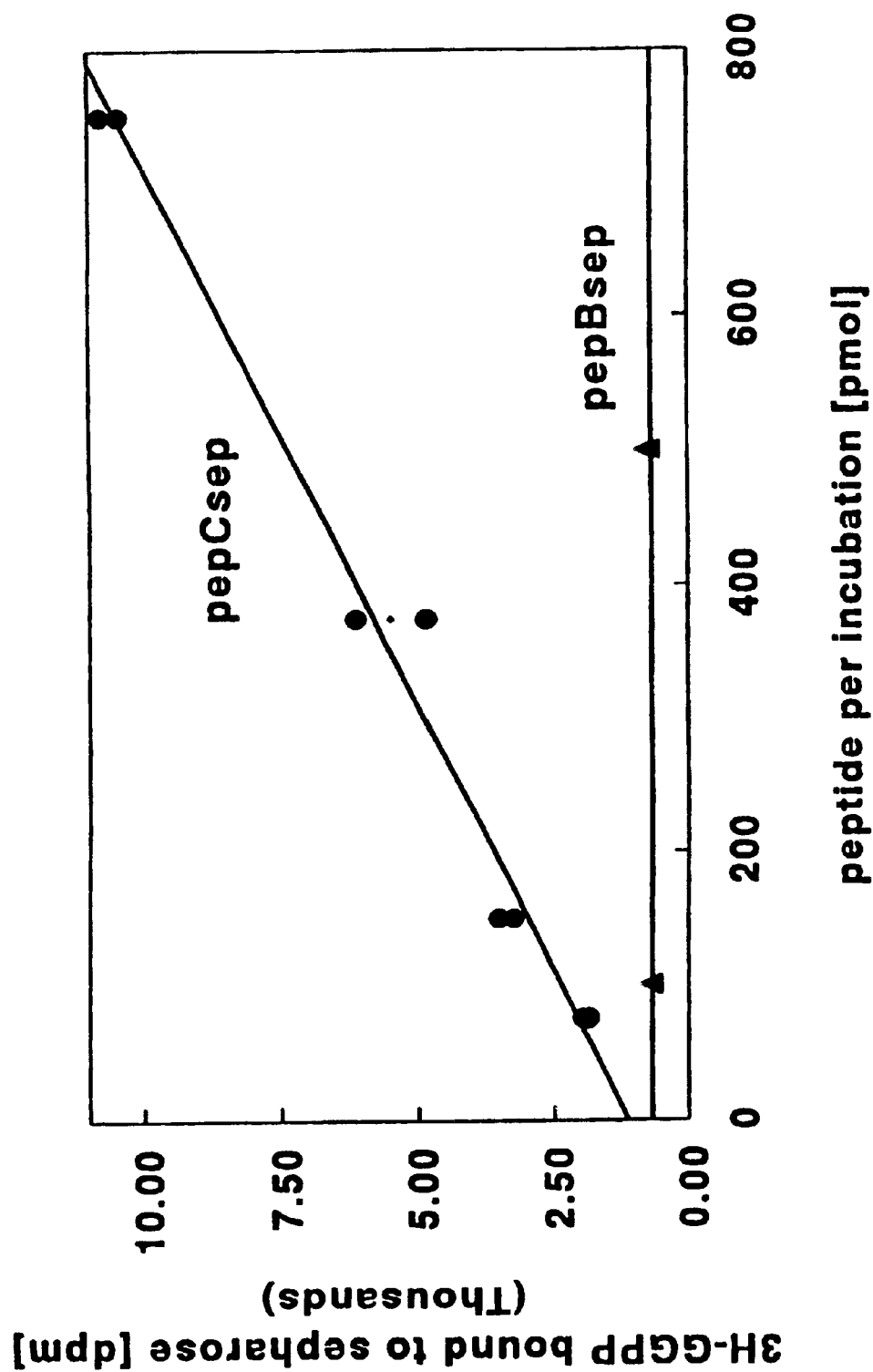

REAGENT AND KIT FOR DETERMINING ISOPRENYLATING ACTIVITY AND INHIBITION THEREOF

This application is a continuation-in-part of application Ser. No. 08/230,522, filed Apr. 20, 1994, now abandoned.

The present invention is in the field of biochemical analysis. In particular, the invention relates to an immobilised oligopeptide and to a kit containing this immobilised oligopeptide for determining protein isoprenylating activity in biological samples.

Mammalian cell proteins can undergo post-translational modification by derivatisation of carboxyl-terminal cysteine residues by mevalonate-derived isoprenyl groups. Several of these isoprenylated proteins were identified as belonging to groups of related proteins: e.g. the nuclear lamins, low molecular weight GTP binding proteins, such as the ras-oncogene proteins and heteromeric G proteins. The polyisoprenyl group that was attached to a protein was identified as farnesyl ($C_{15}$) or geranylgeranyl ($C_{20}$), depending on the recognition of the C-terminal amino acid sequence of the proteins involved. Lamins and $p21^{ras}$ proteins, which possess the consensus CAAX motif (C=cysteine, A=any amino acid having an aliphatic side chain and X=any amino acid), are farnesylated, while several members of the rab proteins having C-terminal CC or CXC motifs, and of the heteromeric G-protein λ-subunits are geranylgeranylated. Reviews of the post=translational modification of proteins by isoprenoids in mammalian cells are given by Maltese W. A. in *FASEB J.* 4 3319–3328 (1990) and Casey P. J. in J. Lipid Res. 33 1731–1740 (1992).

The isoprenylation of these proteins seems to play a role in their association with membranes and nuclear envelopes, where they are processed further and/or perform their function. This was shown for example by blocking the mevalonate synthesis by HMG-CoA reductase inhibitors, which prevented proteolytic processing of the lamin A precursor (Beck et al., *J. Cell. Biol.* 110 (1990) 1489–1499) or resulted, in other studies, in the accumulation of non-isoprenylated $p21^{ras}$ precursor and the loss of transforming activity of oncogenic ras proteins. The latter observation triggered the search for specific inhibitors of the farnesylation of $p21^{ras}$ in order to prevent its action in cells, where overexpression of this protein leads to tumour development, such as in colon carcinomas.

G proteins play a role in the receptor-mediated transduction of signals (such as growth modulation signals) over the plasma membrane, and other isoprenylated proteins, not yet identified, may have a function in cell cycle progression. There is evidence as well that GTP binding proteins are involved in the regulation of intracellular protein traffic and secretion. There is even some suggestion that isoprenylated proteins play a role in the translational control of HMG-CoA reductase, the rate limiting enzyme of the isoprene and subsequent cholesterol synthesis.

The enzymes involved in the protein isoprenylation process, protein:prenyl transferases, are reported to use either all-transfarnesyl pyrophosphate (FPP), as a substrate for the addition of the farnesyl group to the protein, or geranylgeranyl pyrophoshpate (GGPP), as a substrate in the production of geranylgeranylated proteins.

In the present description, the terms prenyl and isoprenyl are both used to denote hydrocarbon groups containing a plurality of branched, unsaturated $C_5$-moieties, in particular hydrocarbons containing 2 to 6 of such methyl-butenylene groups, including farnesyl and geranylgeranyl groups. Similarly, the terms isoprenylation and prenylation are used indiscriminately to denote the transfer of such hydrocarbon groups.

In view of the importance of protein isoprenylation in biological processes, it is an object of the present invention to provide a reliable diagnostic reagent to determine protein isoprenylation (prenyl-transferase) activity. A further object is to provide a reagent which allows the isolation and identification of enzymes having protein isoprenylation activity. Another object is to provide a reagent for the screening of inhibitors of this process. The invention is also aimed at providing kits and methods comprising such reagents.

These objects are achieved by an immobilised oligopeptide for detecting protein isoprenylation, consisting of an oligopeptide containing the amino acid sequence Xad-Xac-Xab-Xaa-OH at its carboxyl-terminus, at least one of Xaa, Xab, Xac and Xad representing cysteine (Cys), said sequence being capable of reacting with a prenyl transferase catalysing the protein isoprenylation, and being bonded at its amino-terminus to a solid carrier.

A preferred aspect of the invention is a kit for detecting or identifying protein isoprenylation activity comprising the immobilised oligopeptide as described above, together with a prenyl pyrophosphate, and a marker.

The immobilised oligopeptide and the kit according to the invention allow a reliable, convenient and rapid detection of protein prenylation activity, a rapid detection, characterisation and isolation of enzymes having protein prenylation activity, as well as of inhibitors of such enzymes, and a localisation of prenylation activity in a particular tissue and a discrimination between various types of protein prenylation, e.g. farnesylation and geranylgeranylation.

In a preferred group of oligopeptides according to the invention having the amino acid sequence Xad-Xac-Xab-Xaa-OH, Xad represents cysteine. The amino acids Xaa, Xab, and Xac may vary, depending on the particular type of enzymic activity to be diagnosed. When detecting or identifying protein farnesylation, the amino acid Xaa preferably represents Met, Gln, Ala or Ser, most preferably Leu.

In the amino acid sequence described above Xab and Xac, and especially Xab, preferably represent aliphatic amino acids. In the present description, aliphatic amino acids are understood to comprise 2-aminoalkanoic acids having about 2 to 8, in particular 3 to 6 carbon atoms. These include natural amino acids, such as glycine (Gly), alanine (Ala), valine (Val), leucine (Leu) and isoleucine (Ile), and also proline (Pro), but also non-natural amino acids such as α-aminobutyric acid (Abu), α-aminoisobutyric acid (Aib), norvaline (Nva), norleucine (Nle) and 2-aminoheptanoic acid (Ahe). Preferred aliphatic amino acids are Ala, Val, Ile and Leu.

In another preferred group of oligopeptides according to the invention having the amino acid sequence Xad-Xac-Xab-Xaa-OH and susceptible to geranylgeranylation, Xaa represents cysteine. In addition to this, either Xab or Xac preferably represents cysteine as well, thus constituting the terminal motifs CC and CXC respectively of the rab/YPT1 family. These oligopeptides may advantageously contain other amino acids of the natural substrates of the corresponding prenyl (geranylgeranyl) transferase.

The oligopeptide comprises at least 4 amino acids. The upper limit of the number of amino acids is less critical and is largely determined by practical considerations. In general a sequence of up to about 40 amino acids, or up to 20 amino acids, will be satisfactory, but shorter or longer sequences may also be used. The amino acids situated between Xad and the solid carrier may or may not correspond to those of the natural proteins capable of being isoprenylated. The amino acid bordering Xad may thus be Pro, Arg, or Lys, as in proteins of the ras family, but it may also be a different amino acid. Examples of suitable amino acid sequences are listed by Maltese W. A. (FASEB J. 4 (1990) 3319–3328).

The synthesis of the oligopeptides according to the invention and the coupling thereof to the solid carrier can be performed according to any one of several methods that are known to the skilled person. A suitable example of the synthesis and coupling of oligopeptides is given in EP-A-347,959. The mercapto group of the cysteine residue to be incorporated in the oligopeptide is protected during synthesis, e.g. by an alkylthio group, glutathione or an other protecting group known for that purpose.

The solid carrier can be of various types, such as solid carbohydrates and derivatives thereof, Sepharose, synthetic polymers, such as polystyrene, polyamide, polytetrafluoroethylene, poly(vinylidene difluoride), polycarbonate etc. The carrier may also be inorganic such as glass, silicon, modified silicon, silicon oxide, silicon nitride, gallium phosphide, gallium arsenide, and the like. The carrier can have different shapes such as spheres, granules, filters, strands, pads, slices, films, capillaries, gels, or walls of a microtiter plate.

Coupling of the oligopeptide to the solid carrier may be effected using a linker, such as dialdehydes, diimides, dithiols and the like. Advantageously, the oligopeptide is bonded through activation of the carrier material, e.g. by CNBr activation of a carrier gel, for coupling to primary amino groups, epoxy activation for coupling to hydroxy groups or amino groups, thiopropyl activation for coupling to thiol groups, etc. Suitable examples of carrier materials containing linked functional groups and capable of coupling with free amino groups are CH-Sepharose 4B, which contains 6-carboxyhexylamino groups attached to Sepharose 4B and Activated CH-Sepharose 4B, which contains N-hydroxysuccinimidyl esters of 6-carboxyhexylamino groups attached to Sepharose 4B.

The oligopeptide and the carrier may be coupled through a spacer that ensures an optimum distance between the carrier and the reactive part of the oligopeptide. The spacer may first be bound to the carrier or to the oligopeptide before the immobilised oligopeptide is formed. A useful example of a spacer is an ω-aminoalkanoic acid, such as ε-aminocaproic acid, used as N-terminal group of the oligopeptide. As an alternative, the linker group referred to above, which provides for coupling of the oligopeptide to the carrier, may also serve as a spacer.

In the kit according to the invention, the immobilised oligopeptide described above is a substrate for a protein isoprenylation reaction. The kit preferably further contains a source of the appropriate isoprenyl groups, in particular an isoprenyl (prenyl) pyrophosphate. Examples of isoprenyl pyrophosphate are farnesyl pyrophosphate and geranylgeranyl pyrophosphate. Thus, the kit contains the essential reagents for performing an assay of protein isoprenylation enzyme activity of a sample. The kit may also contain other reagents to be used in the assay, such as alkaline earth metal ($Mg^{2+}$, $Ca^{2+}$) solutions, etc.

Preferably, the kit according to the invention further contains a control reagent to be used as a blank in the protein isoprenylation assay. Suitably, this reagent is an immobilised oligopeptide which differs from the substrate immobilised oligopeptide in that the cysteine residue is substituted by another amino acid. This other amino acid can be any natural or non-natural amino acid lacking the mercapto group which is essential for protein isoprenylation, for example alanine, α-amino-butyric acid or serine. The other amino acid can also be a cysteine, the mercapto group of which is blocked, e.g. by an alkylthio group. This control reagent allows for correction of any aspecific isoprenylation, and is especially useful for quantitative assays.

The kit according to the invention can also be used for assaying inhibition of protein isoprenylation reactions, in particular inhibition of protein isoprenylation enzymes. In this embodiment, the kit further contains an enzyme capable of catalysing protein isoprenylation (protein:prenyl transferases). In particular it can contain an enzyme, the inhibition of which is under investigation. The protein isoprenylating enzyme may be a pure enzyme, such as protein:farnesyl transferase or protein: geranylgeranyl transferase. The enzyme may also be contained in a suitable enzyme preparation such as reticulocyte lysate.

The kit may contain the necessary components for carrying out an assay for one type of prenylation activity or inhibition thereof, but also for the combined assay of a plurality of prenylation activities, e.g. both for protein farnesylation and protein geranylgeranylation. In the latter case, the kit will contain several immobilised oligopeptides which are each specific for one type of prenylation, each one preferably accompanied by its own control (i.e. Cys-substituted) oligopeptide.

The kit according to the invention also contains a marker for detecting the occurrence of protein isoprenylation. The marker may be a conventional label, such as a radioactive isotope, a luminescent lable, an avidine/biotine reagent, or an enzyme such as horseradish peroxidase. The marker may be associated with the isoprenyl pyrophosphate. It can e.g. be a radioactive isotope in the isoprenyl group of the isoprenyl pyrophosphate, such as $^3$H-farnesyl pyrophosphate. The marker may also be an antibody, in particular an antibody to the coupling product of the oligopeptide described above and the isoprenyl group. Such an antibody may be labelled, or may be detected in a further immunoreaction. The kit may comprise several antibodies, directed at different prenylated oligopeptides, depending on the type(s) of determination for which the kit is devised.

The invention also relates to the antibodies to the prenylated oligopeptides as explained above. The antibodies according to the invention are preferably monoclonal antibodies. The monoclonal antibodies can be produced by methods commonly known in this art, using the oligopeptides described herein as antigens. An example of a procedure for production and screening of monoclonal antibodies according to the invention, is as follows.

Procedure for production and screening of monoclonal antibodies for farnesylated peptides and proteins.

In order to obtain antibodies for farnesylated proteins and peptides, e.g. the immobilized peptides after farnesylation as mentioned herein, these antibodies should specifically react with the farnesyl-cysteine group of these peptides or proteins. Therefore we decided to start from S-farnesyl-cysteine.

Synthesis of S-farnesyl-cysteine and its Ata-derivative:
Cystein-HCl was dissolved in methanol and the PH adjusted to 10 by addition of diisopropylethylamine. An equimolar quantity of farneysl bromide was added slowly. The progress of the reaction was analyzed by TLC (t-BuOH:AcOH:water, 10:9). After the reaction was finished toluene was added and the solvent evaporated.

Thereafter S-farnesyl-cysteine was derivatized for protein-coupling with the S-acetylthioacetyl-group (Ata) using N-Ata-succinimide (Ata-Su). To this end S-farnesyl-cysteine was dissolved in 50% of dioxane, pH adjusted to 9.5 with diisopropylethylamine and an equimolar quantity of Ata-Su in dioxane was added. After the reaction was finished dioxane was evaporated and the residue acidified. The remaining oil was washed, dried and lyophilized.

b) Preparation of immunogen:
N-Ata-S-farnesyl-cysteine was coupled to bovine serum albumin (BSA). To this end, this protein was functionalized using 6-(1maleimido) hexanoic acid 1-succinimidyl ester as described previously (Peeters et al., Comparison of four bifunctional reagents for coupling peptides to proteins and the effect of the three moieties on the immunogenicity of the conjugates, J. Immunol. Meth. 120 (1989) 133–137; Schielen et al., The sequence of $_\lambda$-(312–324) is a fibrin specific epitope, Blood 77 (1991) 2169–2173).

The acetylthioacetyl moiety of the Ata-farnesylcysteine was activated by cleaving the ethyl-group in 4N NaOH, followed by neutralization with acetic acid, yielding a reactive thioacetyl at the amino-group. Thus activated S-farnesyl-cysteine was added to the freshly functionalized carrier protein in a 30-fold molar excess and allowed to react for 4 h at room temperature. The conjugated protein/farnesyl-cysteine was dialyzed against 0.01M phosphate, 0.14M NaCl, pH7.4 (PBS) and stored at −20° C.

c) Monoclonal antibody production
Female BALB/c mice are immunized with the immunogen and splenocytes are immortalized by fusion with a myeloma cell line according to standard procedures and essentially as described previously (Bos et al., Production and characterization of a set of monoclonal antibodies against tPA, Fibrinolysis, 6 (1991) 173–183). Proliferating hybridoma cells are screened for antibody production in a screening EIA as described below.

d) Assessment of antibody production (screening EIA):
In order to screen for antibody production specific for farnesylated proteins, non-farnesylated recombinant Ha-ras protein and the same protein after in vitro farnesylatin is used. Non-farnesylated recombinant Ha-ras protein was obtained according to Khosrayi-Far and Der (Prenylation analysis of bacterially expressed and insect-expressed Ras and Ras-related proteins, Meth. Enzymol. 255 (1995) 46–59) using the ras-cDNA-containing expression plasmid pAT-rasH.

This protein was farnesylated by the in vitro enzymatic reaction with farnesyl pyrophosphate using the protein-:farnesyl transferase isolated from bovine (Inhibition of purified p21$^{ras}$ farnesyl:protein transferase by Cys-AAX tetrapeptides, Cell 62 (1990) 81–88). The farnesylation reaction was performed essentially according to Reiss et al. The farnesylated or non-farnesylated (negative control) ras-protein are immobilized to microtiter plates. Hybridoma culture supernatants are diluted in PBS/0.1% Tween 20 (PBST), added to the wells and incubated for 2 h at room temperature. Antibody binding is assessed using horseradish peroxidase labelled polyclonal goat anti-mouse and peroxidase-chromogenic substrate mixture TMB/$H_2O_2$ as described by Bos et al. (3,3',5,5'-tetramethyl benzidine as an Ames test negative chromogen for horseradish perioxidase, J immunoassay 2 (1981) 187–204). In this way clones are selected which produce monoclonal antibodies that are reactive on the immobilized farnesylated ras-protein and not reactive on the non-farnesylated ras-protein.

The utility of the kit according to the invention is exemplified below; other uses are also comprised by the invention:

Determination of protein:farnesyl transferase activity in different cells, tissues, body fluids and subcellular fractions.

Assay for isolation and characterisation of different enzymes or isoenzymes, e.g. in cell homogenates, organelles, homogenated other tissue, body fluids, etc.

Using different peptides for the determination of protein:geranylgeranyl transferase.

Screening of inhibitors of the protein-isoprenylation reaction.

As a column material in peptide-affinity column chromatography procedures for enzyme (or enzyme subunit) isolation and purification.

EXAMPLE 1

(i) Synthesis of peptides to be used in the isoprenylation reaction

Using 9-(fluorenylmethyl)oxycarbonyl (Fmoc) derivatives of the appropriate amino acids, peptides were synthesized by means of a semi-automatic solid-phase peptide synthesiser (Labortek, Bubendork Switzerland) using dicyclohexyl carbodiimide/8-hydroxybenzotriazole. The solid phase was 1% cross-linked 4-(hydroxymethyl) phenoxymethyl-polystyrene (Wang resin) charged with about 1 mmol/g of a Fmoc-methionine derivate. After each acylation step the Fmoc group of the peptide was cleaved with piperidine.

Three peptides were synthesized, which had the following amino acid sequences:

Peptide A (derived from the C-terminus of human pre-p21$^{N\text{-}Ras}$)

(SEQ ID NO: 1)
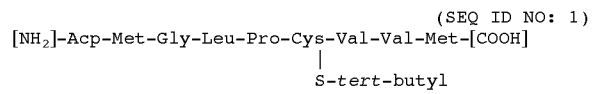

Acp (=ε-aminocaproic acid) was introduced for providing a unique amino group suitable for conjugation to a support, and as an additional spacer. The thiol group of the cysteine residue was protected by a tert-butylthio group, which was removed after coupling to Sepharose.

Peptide B (control peptide with Cys replaced by Ala)
[NH$_2$]-Acp-Met-Gly-Leu-Pro-Ala-Val-Val-Met-[COOH]
(SEQ ID NO: 2)

Peptide C (the same as peptide A, but with C-terminal methionine replaced by leucine as a substrate for geranylgeranylation (Kinsella, B. T., Erdman, R. A. and Maltese, W. M., Proc. Nat. Acad. Sci. 88 (1991) 8934–8938).

(SEQ ID NO: 3)
[NH$_2$]-Acp-Met-Gly-Leu-Pro-Cys-Val-Val-Leu-[COOH]
                              |
                         S-tert-butyl (ii) Coupling of peptides to a solid phase Peptides A, B and C were coupled to activated CH-Sepharose 4B beads through the free NH$_2$ group according to the procedure as described by the manufacturer (Pharmacia). 0.8–5 nmol of the peptides were coupled to 1 μl of Sepharose gel. The material was stored in 0.5M NaCl-0.1M Tris/HCl (ph 8) –20% ethanol at 4° C.

Before use the tert-butylthio group was removed from peptides A and C by resuspending the Sepharose beads in 10 mM DTT (dithiothreitol).

(iii) Quality control and quantification of coupled peptides

The quantity of peptides coupled to the Sepharose beads was determined by C-terminal amino acid analysis. 10 μl of washed peptide A-, peptide B-, peptide C-Sepharose (pepAsep, pepBsep, pepCsep, resp.) or beads without peptide (control) were resuspended in 200 μl of 0.2M of N-ethyl-morpholinium acetate (pH 8.0) containing 1 mg/ml prewashed Carboxypeptidase A (Serva) and 1 mM phenylmethylsulfonyl fluoride (as serine protease inhibitor). Incubation was performed for 20 h at 25° C. with continuous shaking. After centrifugation (1 min; 13,000 rpm) the supernatant, containing the C-terminal amino acids, was lyophilised. These amino acids were quantitated using an automated amino acid analyser. The minor quantities of amino acids present in the supernatant of the control incubation (from autodigestion of Carboxypeptidase A) were subtracted from the values obtained with the peptide-coupled Sepharoses. Only either valine and methionine (pepAsep and pepBsep) or valine and leucine (pepCsep) were detected and the molar ratio of valine to methionine/leucine was 2 to 1 in all cases. From the absolute values the quantity of pmol peptide bound to Sepharose was calculated, which was in the range of 0.8–5 μmol of peptide/ml of Sepharose.

EXAMPLE II

Assay of protein:farnesyl transferase activity in rabbit reticulocyte lysate

Commercially available rabbit reticulocyte lysate contains enzymes necessary for protein-isoprenylation, such as protein:farnesyl transferase activity (Vorburger, K., Kitten, G. T. and Nigg, E. G., EMBO J. 8 (1989) 4007–4013) and protein:geranylgeranyl transferase (Maltese, W. A. and Robishaw, J. D., J. Biol. Chem. 265 (1990) 18071–18074). Using pepAsep (example I) as substrate and pepBsep (example I) as control the assay of protein:farnesyl transferase activity was performed as follows: In 25 μl of a mixture containing 5 μl of pepAsep or pepBsep (both containing an equal quantity of peptide), 13 μl rabbit reticulocyte lysate (promega), 0.5 mM MgCl$_2$, 1 mM DTT, 50 mM Tris-HCl (pH 7.4) and [$^3$H]-farnesyl pyrophosphate ($^3$H-FPP; concentration as indicated in the figures; specific radioactivity 15 Ci/mmol; ARC, USA) the incubation was performed at 37° C. for 30 min with continuous shaking. The reaction was terminated by addition of 1 ml 2% SDS, the beads were spun down and washed 3 times with 2% SDS under shaking for 45 min at 50° C. The radioactivity bound to the Sepharose was measured in a Packaged Tricarb liquid scintillation counter.

Several characteristics of the peptide-farnesylation reaction, e.g. the dependency on peptide concentration (at constant quantity of Sepharose beads; FIG. 1A), farnesyl pyrophosphate concentration (FIG. 1B) and incubation time (FIG. 1C), are shown in FIG. 1. From the differences in the results obtained with pepAsep and pepBsep it is clear that the reaction is strongly dependent on the presence of the cysteine residue in peptide A. For the determination of the protein:farnesyl transferase activity the $^3$H-counts bound to pepBsep (background control) are subtracted from the counts bound to pepAsep.

EXAMPLE III

Assay of protein:geranylgeranyl transferase activity in rabbit reticulocyte lysate With pepCsep (example I) and [$^3$H]-geranylgeranyl pyrophosphate ($^3$H-GGPP) as substrates and pepBsep (example I) as control protein:geranylgeranyl transferase activity was detected in reticulocyte lysate. In this example, illustrated in FIG. 2, the 25 μl of incubation mixture contained: 5 μl of pepBsep or pepCsep (containing the indicated quantity of peptide), 13 μl rabbit reticulocyte lysate (Promega), 0.5 mM MgCl$_2$, 1 mM DTT, 50 mM Tris-HCl (pH 7.4) and 0.4 μM $^3$H-GGPP (specific radio-activity 15 Ci/mmol; ARC, USA) the incubation was performed at 37° C. for 30 min with continuous shaking. The reaction was terminated by addition of 1 ml 2% SDS, the beads were spun down and washed three times with 2% SDS with shaking for 45 min at 50° C. The radioactivity bound to the Sepharose was measured in a Packard Tricarb liquid scintillation counter. The dependency of the peptide C concentration is shown in FIG. 2. Only a few dpm were associated with the control pepBsep.

EXAMPLE IV

Test of inhibitors of protein:farnesyl transferase activity in rabbit reticulocyte lysate In this reticulocyte lysate system two farnesyl pyrophosphate analogues (FPPAs), (E,E)-[Hydroxy-(3,7,11-trimethyl-2,6,10-dodecatrienyloxymethylphosphinyl) methyl]phosphonic acid (FPPA1) (Biller S. A. et al., *J. Am. Chem. Soc.* 133 (1991) 8522–8524) and farnesyl phosphonophosphate (FPPA2) (Valentijn, A.R.P.M., Van der Marel, G. A., Cohen, L. H, and Van Boom, J. H., SYNLETT (1991) 664—664) were tested for their potency to inhibit the protein:farnesyltransferase activity. The reaction was performed as described above, using 80 pmol of both peptides/6 μl beads and 0.7 μM $^3$H-FPP, in the presence of various concentrations of FPPA1 or FPPA2. As can be seen in FIG. 3, both analogues are inhibitors of the enzyme reaction.

FPPA2 is more potent (IC$_{50}$-value of 0.29±0.02 $\mu$M) than FPPA1 (IC$_{50}$:5.26±1.10 $\mu$M)

1A) dependency on peptide concentration: 5 $\mu$l of Sepharose containing 0–1000 pmol peptide A or B were incubated for 30 minutes under the conditions indicated in the text; FPP-concentration was 0.7 $\mu$M.

1B) dependency on FPP concentration: 80 pmol of pepAsep or pepBsep/5 $\mu$Sepharose were incubated for 30 minutes with various quantities of [$^3$H]-FPP under the conditions indicated in the text.

1C) dependency on incubation time: 80 pmol of pepAsep or pepBsep/5 $\mu$l Sepharose were incubated for the indicated times in the presence of 0.7 $\mu$M of [$^3$H]-FPP.

FIG. 2 shows the geranylgeranyl transferase activity in reticulocyte lysate; the dependency on the concentration of peptide B or C bound to 5 $\mu$l of Sepharose beads. See Example III.

Figure 1A:
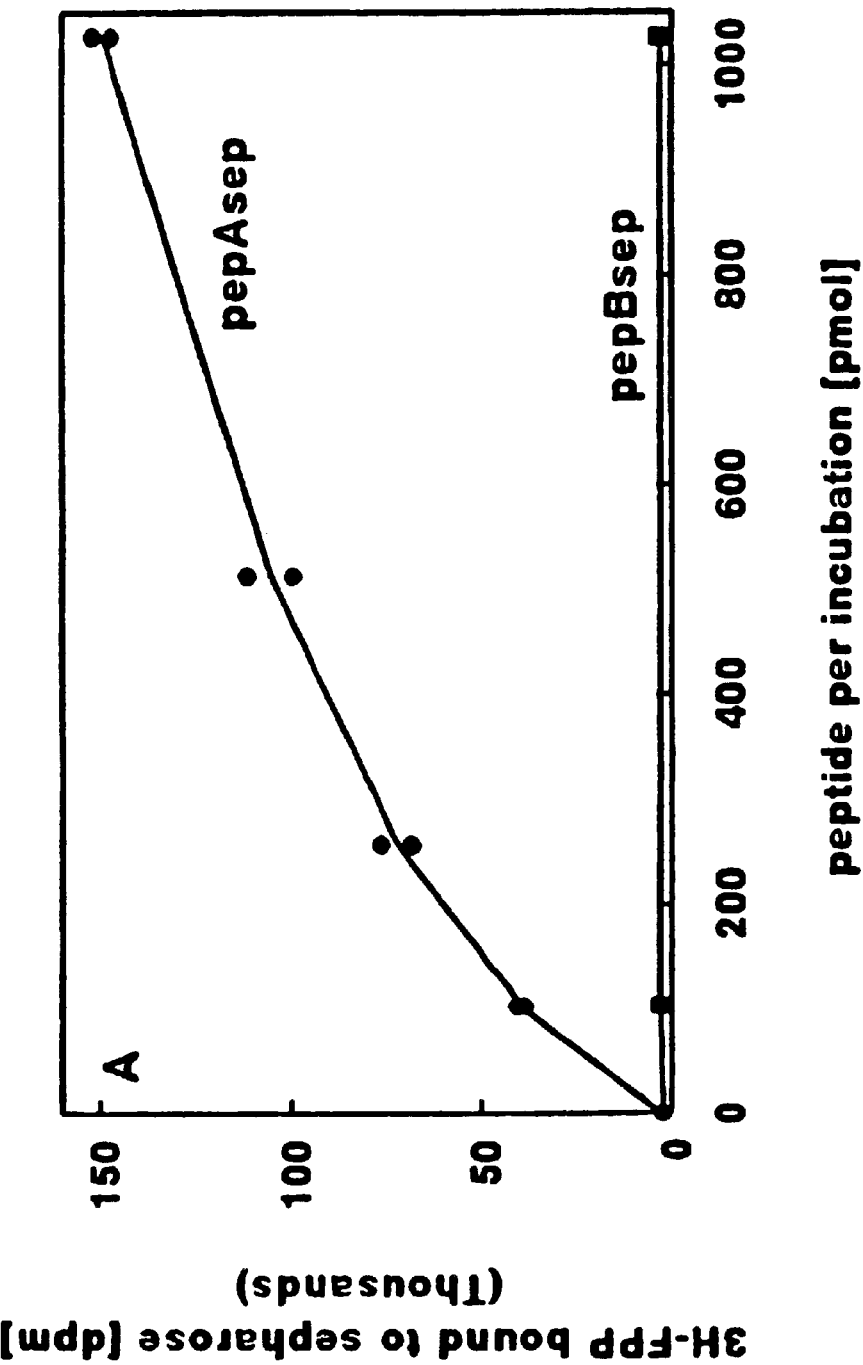
FIGS. 1(A–C) shows the farnesyl transferase activity in rabbit reticulocyte lysate, determined with Sepharose-bound peptide A (pepAsep) and Sepharose-bound peptide B (pepBsep) (see Example II).
Figure 1B:
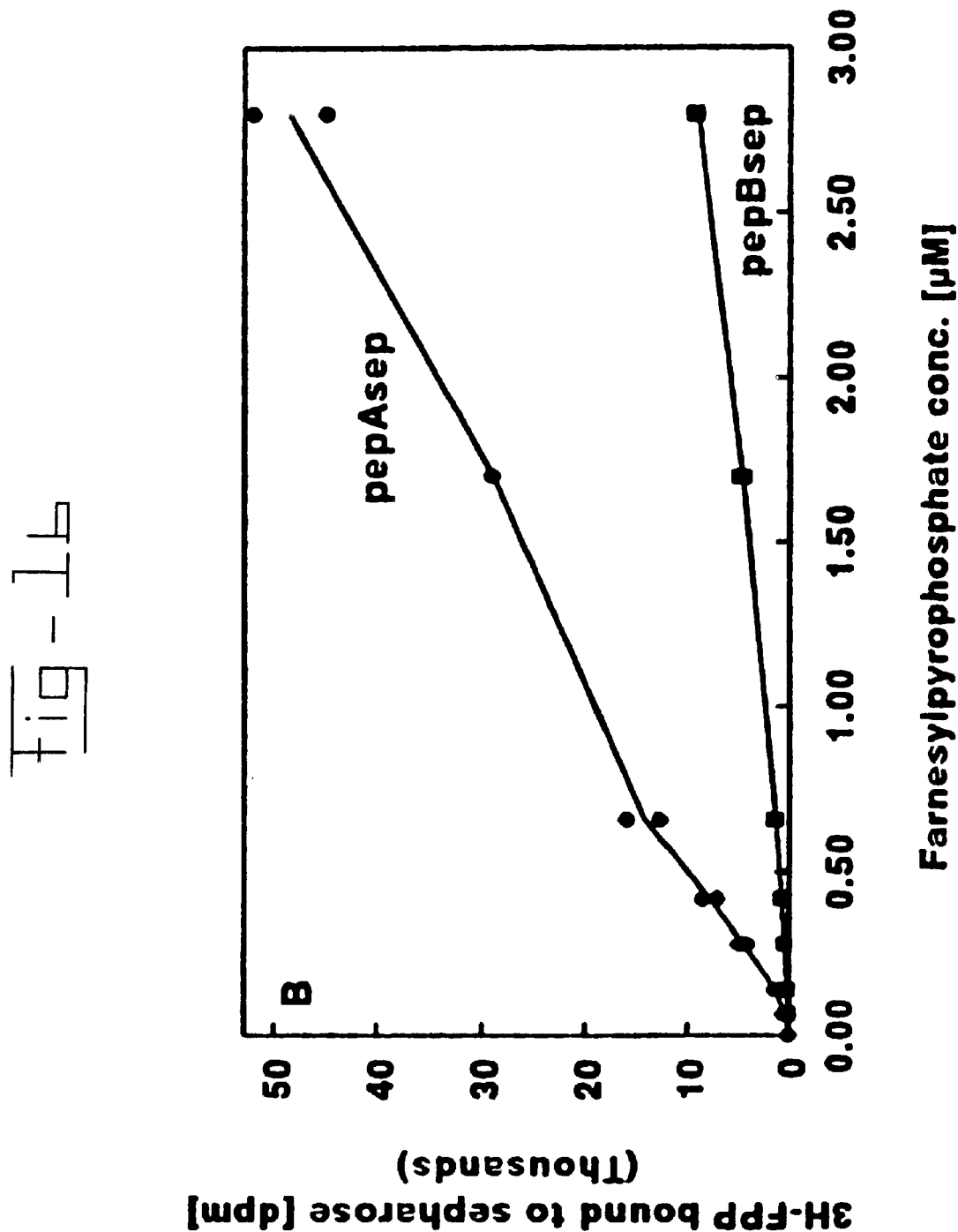
Figure 1C:
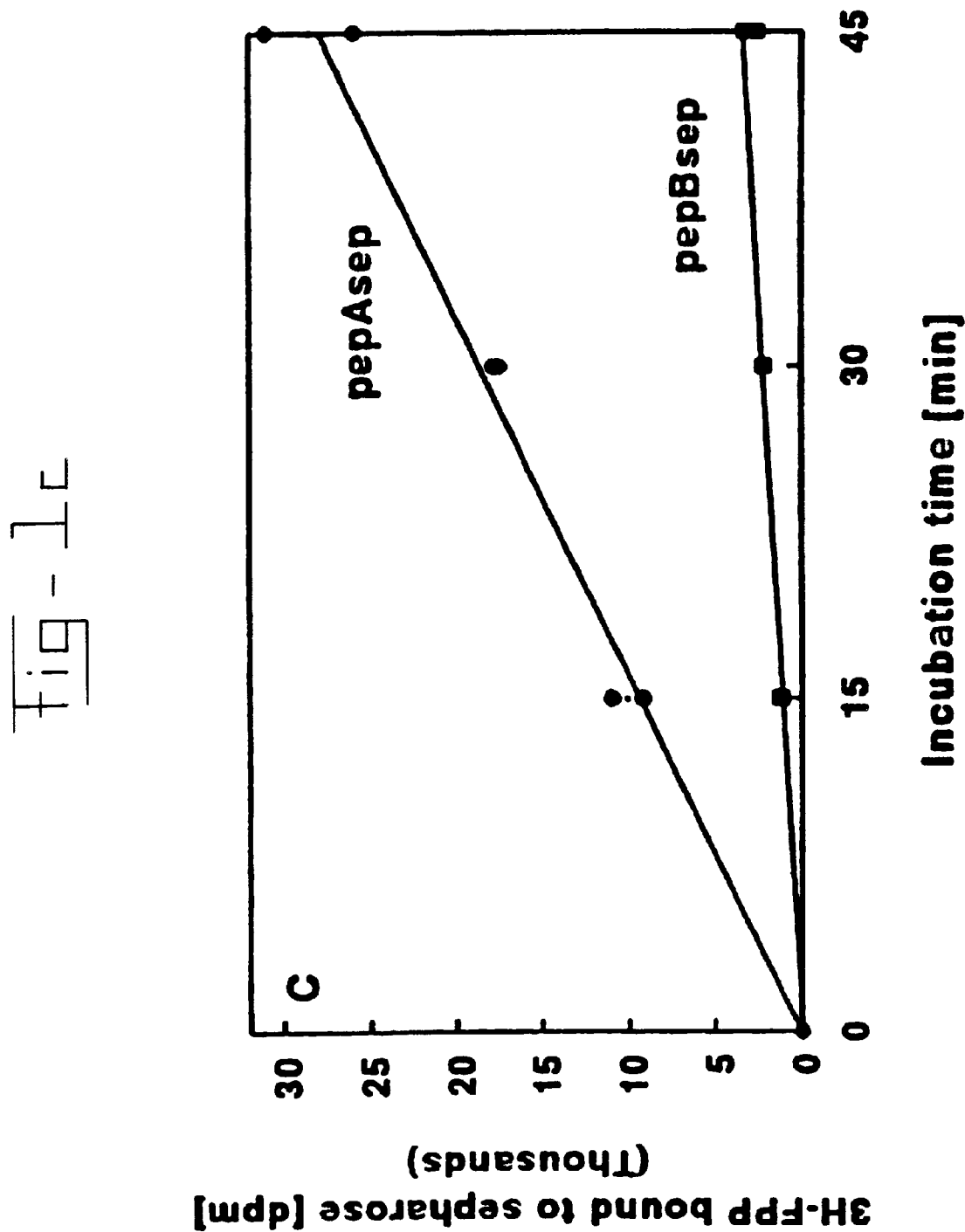
Figure 3:
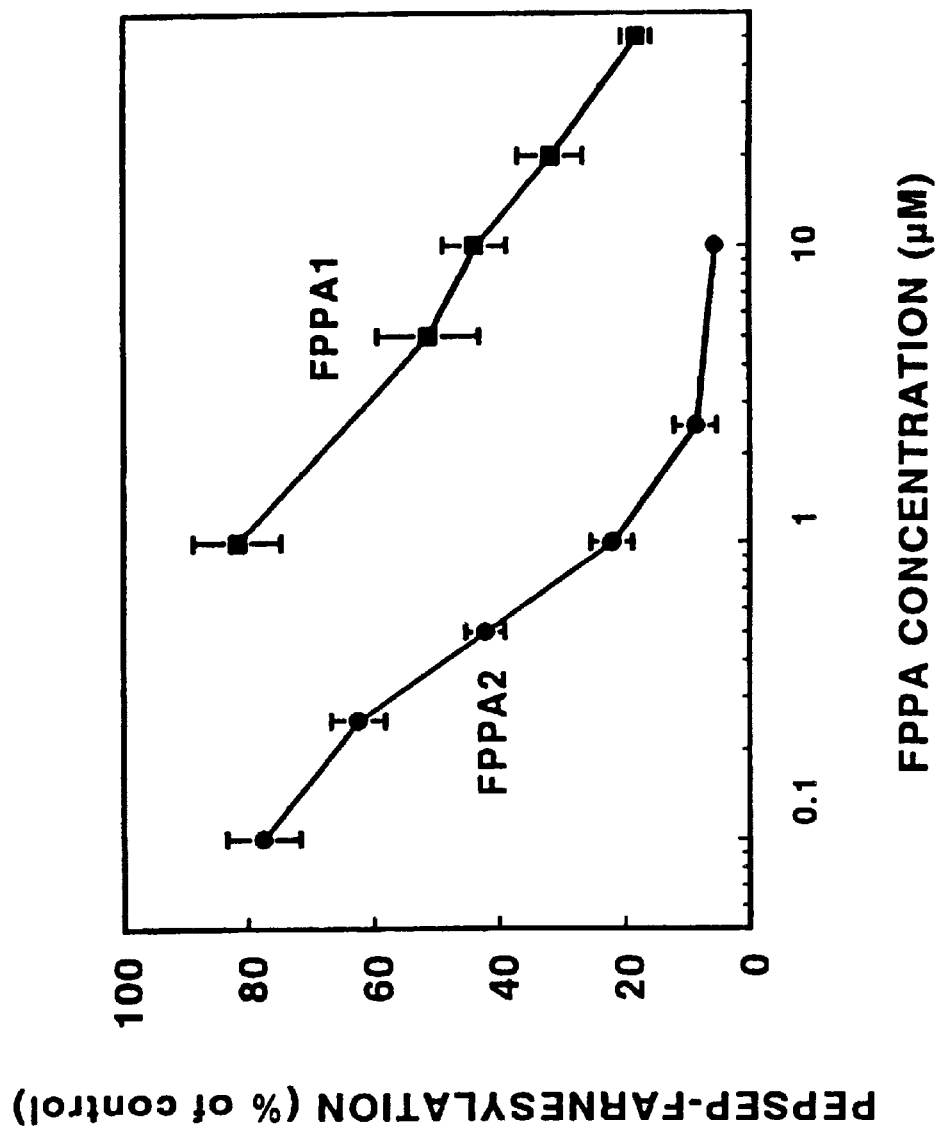

FIG. 3 shows the inhibition of protein: farnesyltransferase in reticulocyte lysate by farnesyl pyrophosphate analogues. 80 pmol of pepAsep and pepBsep/5 $\mu$l Sepharose were incubated for 30 minutes in the presence of 0.7 $\mu$M of [$^3$H]-FPP and the indicated concentrations of the farnesyl pyrophosphate analogues FPPA1 and FPPA2 as mentioned in Example IV. The farnesylation activity was calculated as $^3$H-dpm bound to pepAsep minus the pepBsep-bound-dpm and expressed as percentage of control (without inhibitor).

We claim:

1. A kit for detecting protein prenylation, comprising:

a) an immobilized oligopeptide having from 4 to 40 amino acid residues containing the amino acid sequence Xad-Xac-Xab-Xaa-OH at its carboxyl-terminus, at least one of Xaa, Xab, Xac and Xad representing cysteine (Cys), said sequence being capable of acting as a substrate for a prenyl transferase catalyzing protein prenylation, said oligopeptide being bonded to a solid carrier, and b) a monoclonal antibody which binds the reaction product of farnesyl pyrophosphate or geranylgeranyl pyrophosphate and said oligopeptide but not the oligopeptide.

2. The kit according to claim 1, for detecting protein farnesylation, wherein in said amino acid sequence Xad represents Cys and Xaa represents an amino acid selected from the group consisting of Met, Ser, Gln and Ala.

3. The kit according to claim 1, wherein in said amino acid sequence at least one of Xab and Xac represents an aliphatic amino acid selected from the group consisting of Ala, Val, Ile, Leu, Gly, Pro, Abu, Aib, Nva, Mle and Ahe.

4. The kit according to claim 1, further comprising a prenyl pyrophosphate.

5. The kit according to claim 1, further comprising a second immobilized oligopeptide which differs from said first immobilized oligopeptide in that the cysteine residue is substituted by another amino acid not containing a free thiol group.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:1:

Xaa Met Gly Leu Pro Cys Val Val Met
1                   5

(2) INFORMATION FOR SEQ ID NO:2:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:2:

Xaa Met Gly Leu Pro Ala Val Val Met
1                   5

(2) INFORMATION FOR SEQ ID NO:3:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:3:

Xaa Met Gly Leu Pro Cys Val Val Leu
1                   5